United States Patent [19]

Taoka et al.

[11] Patent Number: 5,079,382
[45] Date of Patent: Jan. 7, 1992

[54] PROCESS FOR THE PRODUCTION OF 3,4-EPOXYBUTYRATE AND INTERMEDIATE THEREFOR

[75] Inventors: Naoaki Taoka, Takasago; Kenji Inoue, Kako; Shigeo Hayashi, Takasago; Noboru Ueyama, Kakogawa; Satomi Takahashi, Kobe, all of Japan

[73] Assignee: Kanegafuchi Chemical Industry Co., Ltd., Osaka, Japan

[21] Appl. No.: 617,345

[22] Filed: Nov. 23, 1990

[30] Foreign Application Priority Data

Nov. 25, 1989 [JP] Japan .................................. 1-305895

[51] Int. Cl.$^5$ .................... C07C 309/04; C07C 309/30
[52] U.S. Cl. ...................................... 560/14; 560/150; 560/11
[58] Field of Search ........................... 560/11, 14, 150

[56] References Cited

U.S. PATENT DOCUMENTS

4,501,704  2/1985  Martel et al. ......................... 560/11
4,966,731  10/1990  Chou ..................................... 560/11

FOREIGN PATENT DOCUMENTS

2406812  8/1974  Fed. Rep. of Germany .
1117855  5/1989  Japan .

*Primary Examiner*—Jane T. Fan
*Assistant Examiner*—Amelia A. Owens
*Attorney, Agent, or Firm*—Wegner, Cantor, Mueller & Player

[57] ABSTRACT

A 3,4-epoxybutyrate of the formula:

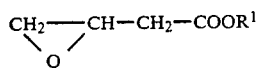

wherein $R^1$ is an alkyl or aralkyl group is efficiently prepared by a process comprising steps of:

(a) reacting 3,4-dihydroxybutyronitrile of the formula:

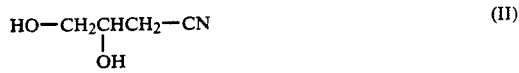

with a sulfonyl chloride of the formula: $R^2$—$SO_2$—Cl wherein $R^2$ is an alkyl group or a phenyl group which may be substituted in the presence of a base to obtain a compound of the formula:

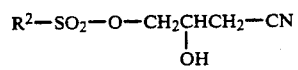

(b) reacting the compound prepared in the step (a) with an alcohol of the formula: $R^1$—OH in the presence of an acid to obtain a compound of the formula:

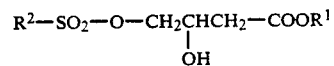

and (c) reacting the compound prepared in the step (b) with a base to obtain the 3,4-epoxybutyrate.

3 Claims, No Drawings

PROCESS FOR THE PRODUCTION OF 3,4-EPOXYBUTYRATE AND INTERMEDIATE THEREFOR

BACKGROUND OF THE INVENTION

1. Field of the Invention

The present invention relates to a process for the production of a 3,4-epoxybutyrate and an intermediate therefor. More particularly, the present invention relates to a process for the production of a 3,4-epoxybutyrate from 3,4-dihydroxybutyronitile and a 3,4-dihydroxybutyric acid derivative which is useful as an intermediate in the production of the 3,4-epoxybutyrate.

2. Description of the Related Art

A 3,4-epoxybutyrate of the formula:

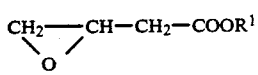
(I)

wherein $R^1$ is an alkyl or aralkyl group is easily converted to carnitine (see U.S. Pat. Nos. 3,830,931 and 3,968,241), which is known as an aperitive and an agent for treating congestive heart failure or arrhythmia (see J. Org. Chem., 53, 104 (1988)).

The 3,4-epoxybutyrate (I) is also known as an important intermediate which can be easily converted to 4-hydroxy-2-oxo-1-pyrrolidineacetamide derivatives including 4-hydroxy-2-oxo-1-pyrrolidineacetamide (oxiracetam) known as an agent for improving cerabral metabolism (see Japanese Patent Kokai Publication Nos. 208957/1985, 461/1987 and 185069/1987).

In addition, the 3,4-epoxybutyrate (I) can be used in the synthesis of $\gamma$-amino-$\beta$-hydroxybutyric acid (GABOB) which has an antiepileptic activity and an antihypertensive activity.

As above, the 3,4-epoxybutyrate (I) is known to be converted to various biologically active substances or medicines.

To prepare the 3,4-epoxybutyrate, the following major processes are known:

(1) A process comprising epoxidizing a vinyl acetate with a peracid (see J. Pharm. Sci., 64, 1262 (1975) and Japanese Patent Kokai Publication No. 10077/1987).

(2) A process comprising methoxycarbonylating epichlorohydrin with carbon monooxide and methanol to obtain a 4-chloro-3-hydroxybutyrate and cyclizing said ester with silver oxide to obtain a 3,4-epoxybutyrate (see J. Org. Chem., 32, 3888 (1967).

However, the first process has problems such as handling of the organic peracid which is inherently corrosive and dangerous in mass scale and the use of heavy metal catalysts such as tungsten.

Since the 3,4-epoxybutyrate (I) has one asymmetric carbon atom in a molecule, it contains two (R)- and (S)-enantiomers and further isomers of the ester (I) include the (RS)-isomer (racemic mixture), (R)-isomer (optically active) and (S)-isomer (optically active).

Recently, utility of optically active substances is increased in various fields such as pharmaceutical, agricultural and liquid crystal fields. By the above process (1), only the (RS)-isomer (racemic mixture) can be produced. Optical resolution of the racemic mixture with an enzyme is known (see Japanese Patent Kokai Publication Nos. 272983/1987 and 272984/1987). However, this optical resolution can provide only the (R)-isomer and the optical purity is unsatisfactory for some alkyl groups of the ester.

By the process (1), no pure (S)-isomer is produced and pure (R)-isomers are produced for some esters. Therefore, it is desired to provide a process for producing both optical active isomers of the 3,4-epoxybutyrate (I).

The above process (2) is not a commercially attractive process because it uses toxic carbon monooxide and produces the product only in a low yield, and silver oxide to be used for cyclization is expensive and should be recovered.

SUMMARY OF THE INVENTION

One object of the present invention is to provide a process for the production of a 3,4-epoxybutyrate, which is economically attractive and easily carried out with good efficiency.

Another object of the present invention is to provide a process for the production of optically active 3,4-epoxybutyrate.

According to the present invention, there is provided a process for the production of a 3,4-epoxybutyrate of the formula:

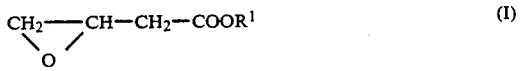
(I)

wherein $R^1$ is an alkyl or aralkyl group, which comprises steps of:

(a) reacting 3,4-dihydroxybutyronitrile of the formula:

(II)

with a sulfonyl chloride of the formula:

(III)

wherein $R^2$ is an alkyl group or a phenyl group which may be substituted in the presence of a base to obtain a compound of the formula:

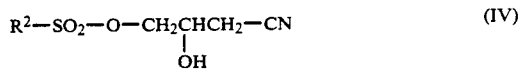
(IV)

wherein $R^2$ is the same as defined above, (b) reacting the compound (IV) obtained in the step (a) with an alcohol of the formula:

(V)

wherein $R^1$ is the same as defined above in the presence of an acid to obtain a compound of the formula:

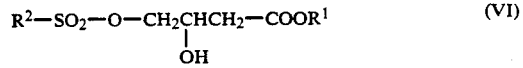
(VI)

wherein $R^1$ and $R^2$ are the same as defined above, and (c) reacting the compound (VI) with a base to cyclize the compound (VI) to obtain the 3,4-epoxybutyrate.

Since each of the compounds (I), (II), (IV) and (VI) has the asymmetric carbon atom at the 3-position, it has the (R)- and (S)-enantiomers.

In the present invention, these compounds include the (R)-isomer, the (S)-isomer, the (RS)-isomer (namely, a racemic compound consisting of a 1:1 mixture of the (R)isomer and the (S)-isomer) and a mixture which contains either one of the (R)-isomer and the (S)-isomer dominantly.

DETAILED DESCRIPTION OF THE INVENTION

Step (a)

The 3,4-dihydroxybutyronitrile (II) as the starting material is a known compound and prepared by one of the processes described in the literature as follows:

The racemic compound 3,4-dihydroxybutyronitrile (II) is prepared by reacting a racemic compound 3-chloro-1,2-propanediol with KCN or NaCN (see J. Am. Chem. Soc., 107, 7008 (1985).

The (S)-isomer of the 3,4-dihydroxybutyronitrile (II) is selectively prepared by reacting (R)-3-chloro-1,2-propanediol, which is effectively prepared through stereo-selective biodegradation of a racemic mixture of 3-chloro-1,2-propanediol (see Japanese Patent Kokai Publication Nos. 122597/1987, 158494/1987 and 36798/1988), with NaCN or KCN under controlled conditions (see Japanese Patent Kokai Publication No. 42050/1990).

The (R) isomer of the 3,4-dihydroxybutyronitrile (II) is prepared from L-ascorbic acid or D-sorbitol through several reactions (J. Am. Chem. Soc., 102, 6304 (1980)).

Then, the 3,4-dihydroxybutyronitrile (II) is reacted with the sulfonyl chloride (III) in the presence of a base.

Herein, $R^2$ is an alkyl group or a phenyl group which may be substituted. Examples of $R^2$ are methyl, ethyl, propyl, isopropyl, butyl, isobutyl, sec.-butyl, pentyl, hexyl, heptyl, octyl, phenyl, p-tolyl, o-tolyl, m-tolyl, xylyl, mesityl and the like. Among them, methyl, phenyl and p-tolyl are preferred. In particular, p-tolyl is preferred.

As the base, any of the conventionally used inorganic and organic bases can be used. Examples of the inorganic base are sodium hydroxide, potassium hydroxide, sodium carbonate, sodium hydrogencarbonate and the like. Examples of the organic base are trimethylamine, triethylamine, tributylamine, pyridine, picoline, lutidine and the like. Among them, pyridine and triethylamine are preferred, in particular, pyridine is preferred. A co-catalyst such as dimethylaminopyridine may be used.

The reaction may be carried out in the absence of an additional solvent. That is, the organic base may be used as a reaction medium. If desired, an organic solvent which does not react with the reagents, in particular the sulfonyl chloride (III) may be used. Examples of such solvent are dichloromethane, ethyl acetate, dioxane, acetonitrile, dimethylformamide, dimethylsulfoxide, chloroform, carbon tetrachloride and the like. Preferably, the reaction is carried out in the absence of a solvent or in the presence of dichloromethane or ethyl acetate.

In the above reaction, 0.5 to 5 moles, preferably 1.0 to 1.5 moles of the sulfonyl chloride (III) and 0.5 to 30 moles, preferably 1.0 to 15 moles of the base are used per one mole of the 3,4-dihydroxybutyronitrile (II). With the sulfonyl chloride (III), preferably an equimolar amount or an excess amount of the base is used.

The reaction temperature is from $-30°$ C. to $+100°$ C. When the solvent is used, a temperature from its melting point to its boiling point can be used. Preferably, the reaction temperature is from $-30°$ C. to $+50°$ C.

The reaction can be completed in from one hour to one day. When the starting material is not consumed completely, additional amounts of the base and the sulfonyl chloride (III) are added.

The reaction can be terminated by pouring the reaction mixture in cooled water or cooled dilute hydrochloric acid, or adding the cooled water or the cooled dilute hydrochloric acid to the reaction mixture. If desired, the solvent or the base may be beforehand evaporated off under reduced pressure. When water is added, it should be sufficiently cooled to prevent side reactions.

After termination of the reaction, the base is optionally removed by washing the reaction mixture with water or acidic water, and the solvent is evaporated off under reduced pressure to recover a crude product. If desired, the crude product is purified by a conventional method such as by using a silica gel column chromatography to obtain the pure 3,4-dihydroxybutyronitrile derivative (IV).

In this step (a), it is possible to selectively produce the reaction on the primary hydroxy group on the 4-position among two hydroxy groups of the 3,4-dihydroxy butyronitrile (II) through control of the reaction temperature and the amounts of the base and the reagents so as to produce the compound (IV) in a good yield.

Step (b)

In the step (b), the 3,4-dihydroxybutyronitrile derivative (IV) obtained in the step (a) is used in the pure form or in the crude form.

The reaction in the step (b) converts the nitrile group in the compound (IV) to the ester group: $COOR^1$. Therefore, any reaction that can covert the nitrile group to the ester group may be used. For example, the nitrile group is first converted to a carboxylic acid group and then converted to the ester group, or the nitrile group is first converted to an imidate group (iminoester) and then converted to the ester group.

Since the compound (IV) has an easily eliminable group ($R^2SO_2$—O—) in the molecule, the conditions are selected that such group is not eliminated. Then, it is preferred that the acid is added to react with the alcohol: $R^1$—OH (V) to form the imidate which is converted to the ester with the addition of water.

Herein, $R^1$ is an alkyl group or an aralkyl group, examples of which are methyl, ethyl, propyl, isopropyl, butyl, isobutyl, sec.-butyl, tert.-butyl, pentyl, hexyl, heptyl, octyl, nonyl, decyl, benzyl, benzyl substituted as in, for example, p-nitrobenzyl, and the like. Among them, methyl, ethyl, propyl, isopropyl, butyl, isobutyl, sec.butyl, tert.-butyl, hexyl and octyl are preferred. Isobutyl is particularly preferred.

As the acid, any of the organic and inorganic acids may be used. Examples are hydrogen chloride, hydrogen bromide, sulfuric acid, p-toluenesulfonic acid, and the like. Among them, hydrogen chloride is preferred.

The reaction is initiated by the addition of the acid to the 3,4-dihydroxybutyronitrile derivative (IV) and the alcohol (V). When the acid is in the gas form, it is bubbled in the 3,4-dihydroxybutyronitrile derivative (IV)

and the alcohol (V). When the consumption of the starting materials is confirmed, water is added to the reaction mixture to convert the product to the 3,4-dihydroxybutyrate derivative (VI).

If desired, the reaction may be carried out in a solvent which is inert to the reaction.

The alcohol (V) is used in an amount of 0.5 to 30 times equivalent, preferably 1 to 20 times equivalent to the compound (IV), and the acid is used in an amount of 0.5 to 30 times equivalent, preferably 1 to 10 times equivalent to the compound (IV).

The reaction temperature is from −30° C. to 100° C., preferably from 0° C. to 50° C.

Under the above conditions, the reaction is completed in about one hour to about 24 hours.

Thereafter, water is added to the reaction mixture in an amount necessary to convert the imidate to the ester and the mixture is heated at 40° C. for one hour to finalize the reaction.

The reaction mixture is separated into two phases. After removing an aqueous phase, an organic layer is neutralized with a base such as sodium hydroxide and again separated. The organic phase is then concentrated under reduced pressure to obtain crude 3,4-dihydroxybutyrate derivative (VI). If necessary, the salt is filtered off, or the product is dried. Further, the product is purified by a conventional method, for example, by using silica gel column chromatography to obtain the pure compound (VI).

In the step (b), the reaction is not influenced by the hydroxy group at the 3-position and the $R^2SO_2$—O— group at 4-position, and the nitrile is converted to the ester in a good yield.

The 3,4-dihydroxybutyrate derivative (VI) is a novel compound which is a subject of the present invention and an important intermediate in the synthesis of the 3,4epoxybutyrate (I) of the present invention.

As stated above, the compound (VI) has an asymmetric center and includes the racemic compound ((RS)-isomer), the (R)-isomer, the (S)-isomer and the mixture of the (R)and (S)-isomers in an arbitrary ratio.

Step (c)

In the step (c), the 3,4-dihydroxybutyrate derivative (VI) obtained in the step (b) is used in the pure form or in the crude form.

In the step (c), the $R^2$—$SO_2$—O— group is eliminated with the base and an epoxy ring is formed at the 3- and 4-positions to obtain the 3,4-epoxybutyrate (I).

The reaction can be carried out in a suitable solvent (e.g. water, hexane, methanol, ethanol, propanol, isopropanol, butanol, isobutanol, sec.-butanol, tert.-butanol, hexanol, octanol, tetrahydrofuran, dichloromethane, chloroform, carbon tetrachloride, ethyl acetate, acetonitrile, dioxane, dimethylformamide, mixtures thereof) or in a two or three phase system.

As the base, any of inorganic and organic bases may be used. Examples of the inorganic base are sodium hydroxide, potassium hydroxide, sodium carbonate, potassium carbonate, sodium hydrogencarbonate, potassium hydrogencarbonate and the like. Examples of the organic base are triethylamine, trimethylamine, tributylamine, pyridine, lutidine, picoline, sodium methoxide, sodium ethoxide, potassium tert.-butoxide and the like.

Since the 3,4-epoxybutyrate (I) is an unstable compound under basic conditions, a combination of the solvent and the base will have a significant influence on a yield of the product. Preferably, the compound (VI) is added to a mixture of hexane and water to produce the reaction in the three phase system, and an aqueous phase is basified with a buffer such as sodium carbonate/sodium hydrogencarbonate, whereby the 3,4-epoxybutyrate (I) is produced in a good yield.

Since by-products and the compound (VI) are hardly soluble in the hexane phase, the product (I) is mainly recovered through separation of the hexane phase after the reaction.

The reaction temperature is from −30° C. to +100° C. When the solvent is used, a temperature from its melting point to its boiling point can be used. Preferably, the reaction temperature is from 0° C. to +80° C.

The reaction time is from 10 minutes to 24 hours, preferably from 10 minutes to 5 hours.

The base is used in an amount sufficient for capturing $R^2SO_2$-OH which is by-produced in the reaction.

After the reaction, water and a solvent necessary for separation are added to the reaction mixture, and the mixture is washed with water. In this post-treatment, the pH of the aqueous phase is neutral or acidic. In such pH range, the stability of the 3,4-epoxybutyrate (I) is increased.

After washing with water, the solvent is evaporated off under reduced pressure to obtain the crude 3,4-epoxybutyrate (I). The crude product can be purified by a conventional method, for example, by using silica gel column chromatography or distillation under reduced pressure to isolate the pure 3,4-epoxybutyrate (I).

In the step (c), the 3,4-epoxybutyrate (I) is selectively produced while suppressing the side reactions.

According to the present invention, the steps (a), (b) and (c) are successively performed to effectively produce the 3,4-epoxybutyrate (I) from the 3,4-dihydroxybutyronitrile (II).

According to the present invention, either optically active substance of the (R)- and (S)-isomers can be freely produced.

PREFERRED EMBODIMENTS OF THE INVENTION

The present invention will be illustrated by following Examples.

EXAMPLES 1

Preparation of (3S)-3-hydroxy-4-p-toluenesulfonyloxybutyronitrile (3S)-3,4-Dihydroxybutyronitrile (43.1 g, 426 mmol), pyridine (240 ml) and tosyl chloride (119.5 g) were mixed at 0° C. for 4 hours. The mixture was poured in ice-cooled 1N hydrochloric acid and stirred, followed by extraction with ethyl acetate. After the organic layer was dried over anhydrous sodium sulfate, the solvent was evaporated off with an evaporator. The residue was purified with silica gel column chromatography (hexane:ethyl acetate=2:1) to obtain (3S)-3-hydroxy-4-p-toluenesulfonyloxybutyronitrile (87.0 g, 340 mmol). Yield, 80 %.

$^1$H-NMR (90 MHz, CDCl$_3$): δ(ppm)=7.82 and 7.40 (d,d, 4H, J=7 Hz), 4.00-4.40 (m, 3H), 3.13 (s, 1H), 2.59 (d, H, J=5 Hz) and 2.48 (s, 3H).

IR (neat): 3500, 2950, 2280, 1600, 1360, 1195 and 1100 cm$^{-1}$.

$[\alpha]_D^{25}$ = −16.62° (c =1.72, ethanol).

EXAMPLE 2

Preparation of
(3S)-3-hydroxy-4-p-toluenesulfonyloxybutyronitrile (3S)-3,4-Dihydroxybutyronitrile (161.8 g, 1.6 mol) was dissolved in pyridine (260 ml). To the resulting solution, a solution of tosyl chloride (396.6 g) in methylene chloride (1.6 liters) was added at 0° C. and stirred at 0° C. for 5 hours. Then, the pH of the mixture was adjusted at 2 with 6N hydrochloric acid, and the mixture was extracted with methylene chloride. After the organic layer was dried over anhydrous sodium sulfate, the solvent was evaporated off. The residue was purified with silica gel column chromatography (hexane:ethyl acetate=2:1) to obtain (3S)-3-hydroxy-4-p-toluenesulfonyloxybutyronitrile (85.9 g). Yield, 70 %.

The physicochemical data were the same as those in Example 1.

EXAMPLE 3

Preparation of
(3R)-3-hydroxy-4-p-toluenesulfonyloxybutyronitrile

In the same manner as in Example 1 but using (3R)-3,4-dihydroxybutyronitrile in place of (3S)-3,4-dihydroxybutyronitrile, the reaction and purification were carried out to obtain (3R)-3-hydroxy-4-p-toluenesulfonyloxybutyronitrile. Yield, 85 %.

The results of $^1$H-NMR and IR analysis were the same as those in Example 1.

$[\alpha]_D^{25} = +16.6°$ (c = 1.72, ethanol).

EXAMPLE 4

Preparation of
(3RS)-3-hydroxy-4-p-toluenesulfonyloxybutyronitrile

In the same manner as in Example 1 but using (3RS)-3,4-dihydroxybutyronitrile in place of (3S)-3,4-dihydroxybutyronitrile, the reaction and purification were carried out to obtain (3RS)-3-hydroxy-4-p-toluenesulfonyloxybutyronitrile. Yield, 78 %.

The results of $^1$H-NMR and IR analysis were the same as those in Example 1.

EXAMPLE 5

Preparation of
(3S)-3-hydroxy-4-methanesulfonyloxybutyronitrile (3S)-3,4-Dihydroxybutyronitrile (8.0 g, 79.1 mmol), pyridine (19.1 ml) and mesyl chloride (7.33 ml) were mixed at 0° C. for 6 hours. The mixture was poured in ice-cooled 1N hydrochloric acid and stirred, followed by extraction with ethyl acetate. After the organic layer was dried over anhydrous sodium sulfate, the solvent was evaporated off with an evaporator. The residue was purified with silica gel column chromatography (acetone:chloroform=5:95) to obtain (3S)-3-hydroxy-4-methanesulfonyloxybutyronitrile (8.1 g). Yield, 57 %.

$^1$H-NMR (CDCl$_3$/acetone-d$_6$): δ(ppm)=4.80 (s, 1H), 4.35 (m, 3H), 3.18 (s, 3H) and 2.78 (d, 2H, J=6 Hz).

IR (neat): 3500, 3050, 2950, 2270, 1420, 1340, 1170, 1110, 1000, 970 and 820 cm$^{-1}$.

$[\alpha]_D^{25} = -6.67°$ (c=8.00, ethanol).

EXAMPLE 6

Preparation of
(3S)-3-hydroxy-4-methanesulfonyloxybutyronitrile (3S)-3,4-Dihydroxybutyronitrile (16.2 g, 160 mmol) was dissolved in pyridine (26.0 ml). To the resulting solution, a solution of mesyl chloride (14.8 ml) in methylene chloride (160 ml) was added at 0° C. and stirred at 0° C. for 6 hours. Then, the pH of the mixture was adjusted at 2 with 6N hydrochloric acid, and the mixture was extracted with methylene chloride. After the organic layer was dried over anhydrous sodium sulfate, the solvent was evaporated off. The residue was purified with silica gel column chromatography (acetone:chloroform=5:95) to obtain (3S)-3-hydroxy-4-methanesulfonyloxybutyronitrile (15.2 g). Yield, 53 %.

The physicochemical data were the same as those in Example 5.

EXAMPLE 7

Preparation of
(3R)-3-hydroxy-4-methanesulfonyloxybutyronitrile

In the same manner as in Example 5 but using (3R)-3,4-dihydroxybutyronitrile in place of (3S)-3,4-dihydroxybutyronitrile, the reaction and purification were carried out to obtain (3R)-3-hydroxy-4-methanesulfonyloxybutyronitrile. Yield, 62 %.

The results of $^1$H-NMR and IR analysis were the same as those in Example 5.

$[\alpha]_D^{25} = +6.67°$ (c=8.00, ethanol).

EXAMPLE 8

Preparation of
(3RS)-3-hydroxy-4-methanesulfonyloxybutyronitrile

In the same manner as in Example 5 but using (3RS)-3,4-dihydroxybutyronitrile in place of (3S)-3,4-dihydroxybutyronitrile, the reaction and purification were carried out to obtain (3RS)-3-hydroxy-4-methanesulfonyloxybutyronitrile. Yield, 65 %.

The results of $^1$H-NMR and IR analysis were the same as those in Example 5.

EXAMPLE 9

Preparation of isobutyl
(3S)-3-hydroxy-4-(p-toluenesulfonyloxy)butyrate

To (3S)-3-hydroxy-4-p-toluenesulfonyloxybutyronitrile (5.0 g, 19.6 mmol), isobutanol (25 ml) was added. Through the mixture, hydrogen chloride gas was bubbled to reach saturation and the mixture was stirred at room temperature for 18 hours. After confirming the consumption of the raw materials with high performance chromatography (reversed phase column: Finepak SILC$_{18-5}$, eluent: acetonitrile/water=1/1), water (25 ml) was added and the mixture was heated at 40° C. for one hour. Thereafter, an aqueous phase was removed from the separated mixture. The organic phase was neutralized with 5N sodium hydroxide, washed with water and concentrated under reduced pressure to obtain a crude product, which was determined with high performance chromatography (reversed phase column: Finepak SILC$_{18-5}$, eluent: acetonitrile/water=1/1) to confirm that isobutyl (3S)-3-hydroxy-4-(p-toluenesulfonyloxy)butyrate was produced in the yield of 95%.

The crude product was purified with silica gel column chromatography (Wakogel C 200, eluent: hexane:ethyl acetate=3:1) to obtain pure isobutyl (3S)-3-hydroxy-4-(p-toluenesulfonyloxy)butyrate as a colorless liquid (6.15 g, 18.6 mmol).

$^1$H-NMR (CDCl$_3$) δ(ppm)=7.3 and 7.80 (dd, 4H, J=8 Hz), 3.94-4.38 (m, 3H), 3.85 (d, 2H, J=7 Hz), 2.96

(s, 2H), 2.51 (d, 2H, J=6 Hz), 2.42 (s, 3H), 1.69-2.15 (m, 1H) and 0.90 (d, 6H, J=6 Hz).

IR (solution in $CH_2Cl_2$) 3600, 2980, 1730, 1380 and 1190 cm$^{-1}$.

$[\alpha]_D^{20}= -1.19°$ (c=2.00, methanol).

EXAMPLE 10

Preparation of isobutyl (3S)-3,4-epoxybutyrate

To isobutyl (3S)-3-hydroxy-4-(p-toluenesulfonyloxy)butyrate (1 g, 3.03 mmol), 1M sodium carbonate buffer (pH 10.8) (10 ml) and hexane (20 ml) were added and heated at 50° C. for 4 hours. Then, the hexane phase was separated and washed with 0.1N hydrochloric acid and with water, followed by concentration under reduced pressure to obtain a crude product. The crude product was determined with gas chromatography (PEG column, 3 mm×2 m, column temperature: 150° C.) to find that isobutyl (3S)-3,4-epoxybutyrate was produced in a yield of 60%.

The crude product was vacuum evaporated (2 mmHg, b.p.: 40-42° C., bath temperature: 70° C.) to obtain pure isobutyl (3S)-3,4-epoxybutyrate as a colorless l $[\alpha]_D^{20}= -22.46°$ (c=2.00, methanol).

$^1$H-NMR (CDCl$_3$): δ(ppm)=3.93 (d, 2H, J=6Hz), 3.45-3.15 (m, 1H), 2.94-2.76 (m, 3H), 2,70-2.48 (m, 3H), 2.22-1.71 (m, 1H) and 0.96 (d, 6H, J=8 Hz)

IR (neat): 2950 and 1720 cm$^{-1}$.

EXAMPLE 11

Preparation of isobutyl (3S)-3-hydroxy-4-methanesulfonyloxybutyrate

To (3S)-3-hydroxy-4-methanesulfonyloxybutyronitrile (5.0 g, 27.9 mmol), isobutanol (25 ml) was added. Through the mixture, hydrogen chloride gas was bubbled to reach saturation and the mixture was stirred at room temperature for 18 hours. After confirming the consumption of the raw materials with preparative thin layer chromatography (silica gel: Gel 60 F-254, developer: chloroform/acetone=1/1), water (25 ml) was added and the mixture was heated at 40° C. for one hour. Thereafter, an aqueous phase was removed from the separated mixture. The organic phase was neutralized with 5N sodium hydroxide, washed with water and concentrated under reduced pressure to obtain a crude product.

The crude product was purified with silica gel column chromatography (Wakogel C 300, eluent: chloroform) to obtain pure isobutyl (3S)-3-hydroxy-4-methanesulfonyloxybutyrate (5.68 g, 22.3 mmol). Isolation yield, 80%.

$[\alpha]_D^{20}= -4.01°$ (c=2.00, methanol).

$^1$H-NMR (CDCl$_3$): δ(ppm)=4.15-4.42 (m, 3H), 3.92 (d, 2H, J=6 Hz), 3.46 (s, 1H), 3.09 (s, 3H), 2.62 (d, 2H, J=6Hz), 1.68-2.22 (m, 1H) and 0.93 (d, 6H, J=6 Hz).

IR (solution in CCl$_4$) 3540, 2980, 1740, 1370 and 1190 cm$^{-1}$.

EXAMPLE 12

Preparation of isobutyl (3S)-3,4-epoxybutyrate

To isobutyl (3S)-3-hydroxy-4-methanesulfonyloxybutyrate (1 g, 3.93 mmol), 1M sodium carbonate buffer (pH 10.8) (10 ml.) and hexane (10 ml.) were added and heated at 50° C. for 1.5 hours. Then, the hexane phase was separated and washed with 0.1N hydrochloric acid and with water, followed by concentration under reduced pressure to obtain a crude product. The crude product was determined with gas chromatography (PEG column, 3 mm×2 m, column temperature: 150° C.) to find that isobutyl (3S)-3,4-epoxybutyrate was produced in a yield of 23%.

The crude product was vacuum evaporated (2 mmHg, b.p.: 40-42° C., bath temperature: 70° C.) to obtain pure isobutyl (3S)-3,4-epoxybutyrate as a colorless l Specific rotation, and the results of 1H-NMR and IR analysis were the same as those in Example 10.

EXAMPLE 13

Preparation of isobutyl (3R)-3-hydroxy-4-(p-toluenesulfonyloxy)butyrate

In the same manner as in Example 9 but using (3R)-3-hydroxy-4-p-toluenesulfonyloxybutyronitrile in place of (3S)-3-hydroxy-4-p-toluenesulfonyloxybutyronitrile, the reaction and purification were carried out to obtain isobutyl (3R)-3-hydroxy-4-(p-toluenesulfonyloxy)butyrate in the yield of 92%.

$[\alpha]_D^{20}= +1.19°$ (c=2.00, methanol).

The results of $^1$H-NMR and IR analysis were the same as those in Example 9.

EXAMPLE 14

Preparation of isobutyl (3R)-3,4-epoxybutyrate

In the same manner as in Example 10 but using isobutyl (3R)-3-hydroxy-4-(p-toluenesulfonyloxy)butyrate in place of isobutyl (3S)-3-hydroxy-4-(p-toluenesulfonyloxy)butyrate, the reaction and purification were carried out to obtain isobutyl (3R)-3,4-epoxybutyrate in the yield of 55%.

$[\alpha]_D^{20}= +22.46°$ (c=2.00, methanol).

The results of 1H-NMR and IR analysis were the same as those in Example 10.

EXAMPLE 15

Preparation of isobutyl (3R)-3-hydroxy-4-methanesulfonyloxybutyrate

In the same manner as in Example 11 but using (3R)-3-hydroxy-4-methanesulfonyloxybutyronitrile in place of (3S)-3-hydroxy-4-methanesulfonyloxybutyronitrile, the reaction and purification were carried out to obtain isobutyl (3R)-3-hydroxy-4-methanesulfonyloxybutyrate in the yield of 75%.

$[\alpha]_D^{20}= +4.01°$ (c=2.00, methanol).

The results of 1H-NMR and IR analysis were the same as those in Example 11.

EXAMPLE 16

Preparation of isobutyl (3R)-3,4-epoxybutyrate

In the same manner as in Example 12 but using isobutyl (3R)-3-hydroxy-4-methanesulfonyloxybutyrate in place of isobutyl (3S)-3-hydroxy-4-methanesulfonyloxybutyrate, the reaction and purification were carried out to obtain isobutyl (3R)-3,4-epoxybutyrate in the yield of 30%.

Specific rotation, the results of $^1$H-NMR and IR analysis were the same as those in Example 14.

EXAMPLE 17

Preparation of isobutyl (3RS)-3-hydroxy-4-(p-toluenesulfonyloxy)butyrate

In the same manner as in Example 9 but using (3RS)-3-hydroxy-4-(p-toluenesulfonyloxy)butyronitrile in place of (3S)-3-hydroxy-4-(p-toluenesulfonyloxy)-butyronitrile, the reaction and purification were carried out to obtain isobutyl (3RS)-3-hydroxy-4-(p-toluenesulfonyloxy)butyrate in the yield of 94%.

The results of ¹H-NMR and IR analysis were the same as those in Example 9.

EXAMPLE 18

Preparation of isobutyl (3RS)-3,4-epoxybutyrate

In the same manner as in Example 10 but using isobutyl (3RS)-3-hydroxy-4-(p-toluenesulfonyloxy)butyrate in place of isobutyl (3S)-3-hydroxy-4-(p-toluenesulfonyloxy)butyrate, the reaction and purification were carried out to obtain isobutyl (3RS)-3,4-epoxybutyrate in the yield of 55%.

The results of ¹H-NMR and IR analysis were the same as those in Example 10.

EXAMPLE 19

Preparation of isobutyl (3RS)-3-hydroxy-4-methanesulfonyloxybutyrate

In the same manner as in Example 11 but using (3RS)-3-hydroxy-4-methanesulfonyloxybutyronitrile in place of (3S)-3-hydroxy-4-methanesulfonyloxybutyronitrile, the reaction and purification were carried out to obtain isobutyl (3RS)-3-hydroxy-4-methanesulfonyloxybutyrate in the yield of 78%.

The results of ¹H-NMR and IR analysis were the same as those in Example 11.

EXAMPLE 20

Preparation of isobutyl (3RS)-3,4-epoxybutyrate

In the same manner as in Example 12 but using isobutyl (3RS)-3-hydroxy-4-methanesulfonyloxybutyrate in place of isobutyl (3S)-3-hydroxy-4-methanesulfonyloxybutyrate, the reaction and purification were carried out to obtain isobutyl (3RS)-3,4-epoxybutyrate in the yield of 35%.

The results of ¹H-NMR and IR analysis were the same as those in Example 10.

What is claimed is:

1. A compound of the formula

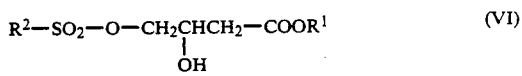

wherein $R^1$ is a $C_1$–$C_{10}$ alkyl, benzyl or nitrobenzyl group $R^2$ is a $C_1$–$C_8$ alkyl, phenyl, o-, m- or p-tolyl, xylyl or mesityl group.

2. A compound according to claim 1 of the formula

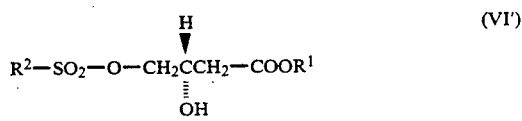

having the (3S)-configuration.

3. A compound according to claim 1 of the formula

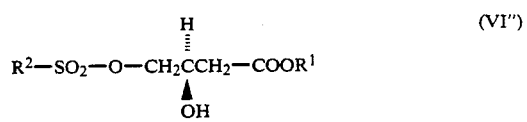

having the (3R)-configuration.

* * * * *